(12) United States Patent
Lee

(10) Patent No.: US 8,522,382 B2
(45) Date of Patent: Sep. 3, 2013

(54) BI-PLANAR ELECTRIC TOOTHBRUSH

(76) Inventor: Soo Woong Lee, Woodland Hills, CA (US)

( * ) Notice: Subject to any disclaimer, the term of this patent is extended or adjusted under 35 U.S.C. 154(b) by 20 days.

(21) Appl. No.: 13/091,875

(22) Filed: Apr. 21, 2011

(65) Prior Publication Data

US 2012/0266398 A1 Oct. 25, 2012

(51) Int. Cl.
*A46B 9/04* (2006.01)
*A46B 13/02* (2006.01)

(52) U.S. Cl.
USPC .................. 15/22.1; 15/22.2; 15/28; 15/110

(58) Field of Classification Search
USPC .................................................. 15/22.1, 105
See application file for complete search history.

(56) References Cited

U.S. PATENT DOCUMENTS

| 5,406,664 A * | 4/1995 | Hukuba | 15/22.1 |
| 6,154,912 A * | 12/2000 | Li | 15/105 |
| 7,404,226 B2 * | 7/2008 | Lee | 15/22.2 |

* cited by examiner

*Primary Examiner* — Monica Carter
*Assistant Examiner* — Stephanie Berry
(74) *Attorney, Agent, or Firm* — John K. Park; Park Law Firm

(57) ABSTRACT

A penetrating electric toothbrush is disclosed, including a handle, a replaceable brush head, a head unit base, an engaging device, a selection device, and an actuator. The replaceable brush head comprises a head body, a plurality of bristles fixed to the head body, and a detachable fastener. The head unit base has a head receptacle portion, a actuator receiving recess, and a bar guiding portion. The reciprocating bar is protruded from the handle and received in the actuator receiving recess, and the actuator receiving recess is configured to engage the reciprocating bar in either penetration mode or polishing mode. The engaging device is disposed at an end of the reciprocating bar and engaging the head unit base with the reciprocating bar. The selection device places the engaging device either in the penetration mode or the polishing mode.

10 Claims, 8 Drawing Sheets

BI-PLANAR ELECTRIC TOOTHBRUSH

BACKGROUND OF THE INVENTION

This invention relates to the field of dental hygiene. Many individuals suffer from periodontal disease. The term "periodontal" is generally defined as the area around the tooth. This includes the gum, periodontal membrane and bone tissue holding a tooth in place. If periodontal disease is diagnosed, dental surgery is typically required to correct the gum condition. Following surgery, it is necessary to keep the space, or sulcus, between the teeth and gum free of any food debris. This is critical for successful healing and improving the gum to a healthy condition.

The healing process following periodontal surgery is critical. Typically, immediately following surgery, the sulcus is filled with temporary protective packing for approximately one to two weeks. Gum swelling resulting from surgery has, after this period of time, subsided to the point where tooth brushing can begin. Dental plaque and food debris must thereafter be kept to a minimum in the sulcus for the gums to continue to heal correctly.

Good oral hygiene for gum healing is one of the most effective dental prophylaxes. For this reason, it is critical to obtain an effective penetration of the toothbrush bristle tips into the sulcus. Despite his wonderful concept, practicality is in question when Dr. Bass method whenever they are related to oral prophylaxis.

Importance of penetration stroke by repeated cam movement works in the same way as an asphalt breaking drill powered by air-compressor. Even if there is certain loading pressure on an area or surface without repeated digging stroke, no mechanical effect or change would occur on that surface.

However, most individuals tend to brush only the prominent tooth surfaces. These surfaces typically do not require brushing and can be adequately cleaned simply by eating fibrous foods such as meats and vegetables.

To properly clean the sulcus, many experts recommend that the bristle tips must reach to the bottom of the sulcus.

Commonly known among dentists is the Bass technique, a method for properly brushing the tooth and sulcus as described in "Glickman's Clinical Periodontology© 1979, pp 729-733". The Bass technique is considered by many dental experts as the most efficient tooth brushing technique; yet most people are either not familiar, or simply don't know how to properly perform this brushing technique.

Proper use of the Bass technique requires a portion of the bristle tips to penetrate into the sulcus with movement of the toothbrush with a short back-and-forth motion without dislodging the tip of the bristles from their position within the sulcus.

The proper method for this technique is that a toothbrush is held using a grip at two points on the brush handle. One point would be the midpoint on the backside of the brush handle, which would be pressed with the index finger. The second point would be on the front side of the handle (same side as the bristles), which the gum-line and slight pressure applied on these two points, and when minimal back and forth motion is applied, the toothbrush will be secure enough in the hand of the user to make the bristles penetrate into the small gum spaces. While performing the above procedure, the user must be able to feel the bristles of the toothbrush with his fingers.

The Bass technique could be more efficiently implemented if a user could insert at least a few of the toothbrush bristle tips to the bottom of the sulcus. Unfortunately, the conventional toothbrush has a high density of bristles so that the result is an ineffective use of the bristles. In other words, bristle density prevents bristles from reaching either the base of the sulcus or deep enough between the teeth spaces.

Despite the fact that the Bass technique is the best brushing technique, it only remains theoretical if user does not determine the proper positioning of the bristles by touch and understand that the bristles need to maintain their linear form for proper penetration. If this is not done, most of the time the bristles will contact the surface of the gum or tooth and simply bend, thus altering the position of the bristle tip and unable to penetrate to the base of the sulcus or deep between the space of adjacent teeth. Using the sense of touch properly, the bristles can penetrate into the small spaces.

When bristles are dragged by generated force such as from side-to-side brushing, bristles cannot maintain its straight and rigid form and, the bristle tips cannot lead into the small spaces due to the exaggerated force and motion applied by the user.

Typical toothbrushes are used to sweep their bristles back and forth across the surfaces of tooth and gum in prophylaxis. In other words, the bristles slide over the small spaces between teeth and between the tooth and the adjacent gum. This sliding action actually causes the bristles to pass over plaque and food debris, or can even force such material deeper into the space.

When a toothbrush is used in this conventional manner, the bristle tips are not properly positioned to be inserted into, nor do they have the necessary contact time within the sulcus to effectively remove plaque and food debris.

SUMMARY OF THE INVENTION

The present invention contrives to solve the disadvantages of the prior art.

An objective of the invention is to provide a penetrating electric toothbrush, which includes a head unit base, an engaging device, and related structures for facilitating installing a replaceable brush head and selecting modes.

Another objective of the invention is to provide a toothbrush where the bristles are not dragged and that will effectively work along the gingival sulcus.

Still another objective of the invention is to provide a toothbrush achieving tooth polishing function by changing the brush axis, thereby changing the direction of movement and function of the bristles.

Still another objective of the invention is to provide a toothbrush where the bristle tips associated with the toothbrush could penetrate deep into the sulcus, contact the base of the gum space and not be dislodged during the implementation of short cleaning.

Still another objective of the invention is to provide a toothbrush that incorporates a small bristle tip surface area on the plurality of the bristles for easy penetration of the bristle tips into the sulcus.

Still another objective of the invention is to provide a toothbrush having reciprocal strokes allowing small number of bristles to move freely.

In order to achieve the above objective, the present invention provides a penetrating electric toothbrush that includes a handle, a replaceable brush head, a head unit base, an engaging device, a selection device, and an actuator.

The handle has an upper portion and a lower portion.

The replaceable brush head comprises a head body, a plurality of bristles fixed to the head body, and a detachable fastener.

The reciprocating bar is provided inside the handle.

The head unit base has a head receptacle portion, a actuator receiving recess, and a bar guiding portion. The reciprocating bar is protruded from the handle and received in the actuator receiving recess, and the actuator receiving recess is configured to engage the reciprocating bar in either penetration mode or polishing mode.

The engaging device is disposed at an end of the reciprocating bar and engaging the head unit base with the reciprocating bar so that the brush head and the head unit base move relative to the reciprocating bar in either penetration mode or polishing mode.

The selection device places the engaging device either in the penetration mode or the polishing mode.

The actuator is disposed inside the handle and moves the reciprocating bar back and forth.

The brush head moves together with the reciprocating bar in the polishing mode. The brush head is free to move relative to the reciprocating bar within a predetermined distance in the penetration mode, and the longitudinal axis of the brush head is inclined from the longitudinal axis of the handle with a predetermined angle. The angled brush head will more effectively activate the bristle tips on the tooth surface for reciprocating strokes either in mode 1 or mode 2, penetrating mode or polishing mode.

The head receptacle portion of the head unit base may be configured to receive, lock, unlock, and release the replaceable brush head.

The handle may comprise a connecting sleeve that is provided on the end of the handle that is adjacent to the selection device, and the selection device comprises: a selection sleeve provided between the handle and the head unit base and surrounding the connecting sleeve of the handle; a selection groove provided inside the selection sleeve; and a selection protrusion that is provided on the connecting sleeve and receives the selection groove.

The selection protrusion may comprise an angularly spaced mode recess that keeps to move the mode change lever; the polishing mode or the penetration mode.

The bar guiding portion may be provided at a lower portion of the head unit base.

The bar guiding portion may provide a cylindrical hole for allowing a portion of the reciprocating bar to move.

The bar guiding portion of the head unit base may comprise a plurality of engaging protrusions on outside, and the plurality of engaging protrusions may be enclosed by the selection sleeve and engage therewith.

The engaging device may comprise an arrow-shaped protrusion, and the actuator receiving recess may comprise a arrow-shaped groove for receiving and locking the arrow-shaped protrusion.

The selection sleeve of the engaging device may further comprise an engaging protrusion, and the handle may further comprise an engaging groove provided around the upper portion of the handle. The engaging protrusion and the engaging groove may connect the selection sleeve and the handle movably.

The selection sleeve of the engaging device may further comprise locking recesses in an upper portion of the selection groove. The selection device may further comprise a locking protrusion that is received by the locking recesses in each mode, by which the locking is achieved. The locking recesses are apart from each other by about 90 degrees as shown in FIG. 9. The locking protrusion is actually provided integrally with the selection protrusion, and may have a shape of a toppled U, which has an elasticity such that the top end is clicked into the locking recesses for each mode. Of course, the locking protrusion may have other shapes having an elasticity vertically, which can be clicked into the locking recess.

The electric toothbrush may further comprise a water proofing rubber sleeve provided around the reciprocating bar in the upper portion of the handle for preventing water from the lower portion of the handle.

The electric toothbrush may further comprise an axis slider ring provided around the reciprocating bar in the upper portion of the handle above the water proofing rubber sleeve for limiting and guiding the movement of the reciprocating bar.

The upper portion of the handle may comprise two or more holes for removing water from inside, and the holes may be provided right above the water proofing rubber sleeve.

The axis slider ring may be made of metal.

The selection sleeve may further comprise an annular gap for allowing an outer portion of the head unit base to move freely and without a pinching gap between the head unit base and the selection sleeve.

The head unit base may further comprise an L-shape fastening groove adapted to fix the replaceable brush head. The detachable fastener is pushed in from the above of, twisted by a predetermined angle (preferably 90 degrees), fit into, and locked with the L-shape fastening groove.

The engaging device comprises a step portion under the engaging device, which prevents it out of the actuator receiving recess.

In certain embodiment of the invention, the selection sleeve may further comprise a mode change lever provided toward inside of the selection sleeve, so as to limit the relative rotation of the selection sleeve and the handle. The mode change lever is stopped by a stopping edge provided in the selection protrusion.

For sake of discussion the direction of brush head movement will be articulated in an x-y-z plane always in relation to the face the bristle tips point to, where y-axis is always defined as the longitudinal axis of the toothbrush, brush head and reciprocating bar.

The brush head is moved to-and-fro substantially perpendicular to the longitudinal y-axis of the brush head with an emphasis that it moves along the x-plane with the bristle tips pointing in the x-axis, and is moved back and forth parallel to the longitudinal y-axis of the brush head simultaneously in the penetration mode. The brush head is moved side-to-side substantially perpendicular to the longitudinal y-axis of the brush head with an emphasis that it moves along the x-plane with the bristle tips pointing in the z-axis, and is moved back and forth substantially parallel to the longitudinal y-axis of the brush head simultaneously in the polishing mode.

The displacement of parallel movement of the brush head in the penetration mode is smaller than the displacement of the parallel movement of the brush head in the polishing mode.

The parallel movement of the brush head in the penetration mode is caused by friction between the reciprocating bar and the actuator receiving recess.

The to-and-fro movement of the brush head in the x-plane in the penetration mode is caused by the inherent oscillatory motion of the reciprocating bar driven through the guide at the open end of the connecting sleeve by the offset cam mechanism.

The parallel y-axis movement, as well as the side to side x-axis movement of the brush head with bristles pointing in the z-axis in the polishing mode follows the movement of the reciprocating bar driven through a guide by an offset cam. In this mode the lock element attached to the brush head is mated to the lock recess in the reciprocating bar and is fixed to move as a singular unit.

The present invention introduces an electric toothbrush that uses a brush head having a reduced number of bristles and that provides two bristle head positions for teeth cleaning. The first is a polishing position for polishing the tooth surface. The second is a penetration position where the bristle head is rotated 90 degrees from the polishing position for reciprocal action of the bristles in a direction into and away from contact with the tooth surface. Stated a different way, the bristle head, when in the polishing position, faces the z-axis and travels substantially along the longitudinal y-axis and perpendicular the x-axis of the toothbrush while the bristle head, when in the penetration position, faces the x-axis and travels substantially along the x-plane perpendicular to the longitudinal y-axis of the toothbrush and a slight parallel motion along the longitudinal y-axis.

The penetration position permits the necessary bristle penetration into the sulcus for effective removal of plaque and food debris lodged within the sulcus and spaces between the teeth.

A key feature of the present invention is recognizing that for the penetration position, allowing the bristle tips to move freely longitudinally as much as possible will minimize any exaggerated force imparted by the user while brushing and allow the bristle tips to vertically align with the small spaces, even if momentarily, and work satisfactorily. The reciprocal action that offsets the short back and forth movement is the best possible method for more efficiently displacing the bristle tips into the spaces between tooth and gum.

Another key feature of the invention is that the user does not have to substantially adjust his grip. By simply rotating the brush head, the user can adjust from a penetration mode to the polishing mode and continue to hold the toothbrush substantially the same way for either mode.

However, it should be noted that in the preferred embodiment the brush head is rotated 90 degrees. The theoretical orientation for using the Bass Method is at a 45 degree angle to the long axis of the tooth; however, in practice with the invention, it is not necessary for the user to regrip or rotate the wrist by as much as 45 degrees, but only to rotate or regrip slightly so that the brush tips are at an angle preferably between 65 to 80 degrees to the long axis of the tooth. The reciprocal penetrating action of the invention does not necessitate the full 45 degree angle mentioned for effective penetration into the gum space.

The reciprocal penetration action of my brush complements the Bass technique discussed earlier.

As stated earlier, my electric toothbrush has two brush head positions: one for polishing and the other for penetration cleaning. In my preferred embodiment, in order to change from one setting to the other, the brush head orientation must be changed relative to the base. Changing the orientation permits the user to hold the toothbrush in substantially the same way for polishing as well as for plaque and food debris removal from the sulcus. Preferably, the brush axis is adjustable by 90 degrees in a left or right turn action.

My invention includes brush tips that are designed to more effectively clean the lingual surface of the anterior and posterior teeth of the lower jaw. The density of the bristle-tips making contact upon the tooth and gum was designed to be less dense than conventional toothbrushes, preferably making rows of bristles that collectively taper.

Preliminary Testing

In preliminary testing which preceded the final design, a standard toothbrush was modified. Specifically, the bristle density was reduced as well as the total surface area occupied by bristles. The result is a brush head that is smaller in area than conventional brush heads with a less dense bristle population. However, patients found it difficult to implement the Bass technique for inserting the bristles into the small space between the tooth and gum.

Additionally, the modified toothbrush could function properly only when the integrity and alignment of the bristles for penetrating into the sulcus were maintained in a substantially straight and rigid form during the application of the pressured strokes of the Bass technique.

In order to function properly, the bristle tips must substantially penetrate to the base of the sulcus. Short strokes in a back-and-forth direction combined with slight pressure into the gum-line are then used while the bristle tips are engaging or digging into the gum area located at the base of the sulcus so that the bristle tips do not slide out of or exit from the sulcus.

After completion of the strokes, the brush is first moved horizontally so the tips dislodge, then moved across to an adjacent area and the same procedure is repeated. A more detailed description of this method now follows:

While the intended results were obtained, the required brushing instructions turned out to be difficult to follow.

Based on the difficulties associated with using bristles rigidly affixed to a brush head to clean the spaces between tooth and gum, a toothbrush was designed with a slidable brush head which is to some degree independent of the brushing movement imparted by the user. This new design tends to maintain the bristles in the correct position for penetration into and cleaning of the sulcus more effectively. My new design not only provides an effective cleaning of the space between tooth and gum but also the polishing of tooth surface when the brush head is adjusted 90 degrees.

Improved Toothbrush Design

My toothbrush has two settings: penetration mode and polishing mode.

Penetration Mode

For this setting, the electric toothbrush displaces the bristle head substantially in a direction perpendicular to the longitudinal axis of the toothbrush along the plane the direction the bristles face. Thus, when the toothbrush is held by the user for brushing, the bristles of the brush head reciprocally move into contact with the teeth and gum. However, because of the rapid vibrational movement as well as the holding position of the toothbrush, it is possible that the bristle tips will not align to the minute contours of the tooth and gum, but will move only according to the limited direction the mechanized cam motion allows, thus not effectively penetrate between the teeth or into the sulcus.

For this reason, it is preferable that the penetration mode includes the ability for the bristle head to freely and slidably move a short distance along the longitudinal axis of the toothbrush that follows or conforms to the contours of tooth surface and gum space the bristles contact. When this feature is incorporated into my invention, the bristles, rather than being bendable when contacting the tooth surface, are able to slide longitudinally a short distance to align with the tooth space and thus remain in a substantially straight condition for deeper penetration between the teeth or into the sulcus or the space between adjacent teeth.

The present invention cleans not only the tooth surface and gum spaces but also effectively manages simple gingivitis (minor gum inflammation). Unlike the bristles found on a conventional toothbrush which are dragged across the tooth surface in a back and forth, or up and down motion following only the mechanized motions of either the user or an electric cam device, the reciprocal toothbrush is designed so that an effective number of bristle tips can penetrate into the sulcus.

My electric toothbrush design incorporates bristles that are cut to form ridges to enhance contact in small area and spaces, provide dual function that is reciprocal and polishable, and control interchangeable direction of stroke by twisting the brush neck with a thumb and index finger.

In the penetration mode, the slidable feature diminishes the bristle resistance associated with the tooth surface. As a result, more bristles are available for penetration into the surrounding crevices and spaces, for more effective removal food debris and other substance from the deep spaces of the sulcus by reciprocal action.

Polishing Mode

The brush head stroke is changed from a penetrating or digging motion to a substantially side-to-side or up-and-down motion in one plane perpendicular to the direction the bristles face. To achieve this change, my preferred embodiment requires that the brush head be rotated relative to the base by 90 degrees.

Also, when the brush head is rotated, it simultaneously locks the position of the brush head preventing the sliding movement that was present for the penetration mode.

Brush head movement substantially along the longitudinal axis of the toothbrush, is typical of' conventional electric toothbrushes and is also the case for my invention. Therefore, for the polishing mode, my toothbrush performs the same function as conventional electric toothbrushes.

This direction of stroke can be used to brush in the traditional manner of sweeping and polishing the prominent tooth surfaces.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE INVENTION

Figure 1:
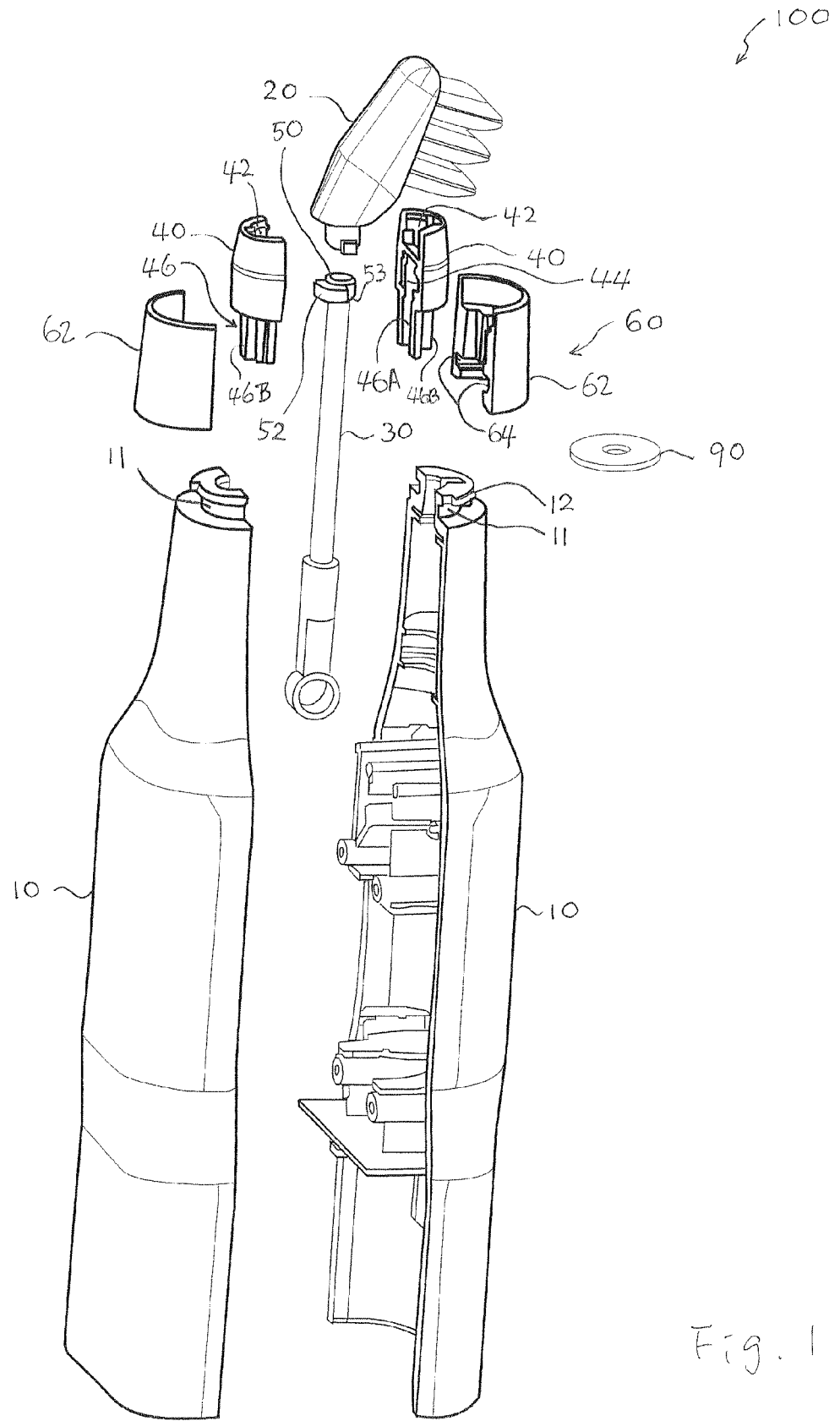
FIG. 1 is an exploded perspective view showing a penetrating electric toothbrush according to an embodiment of the present invention.
Figure 2:
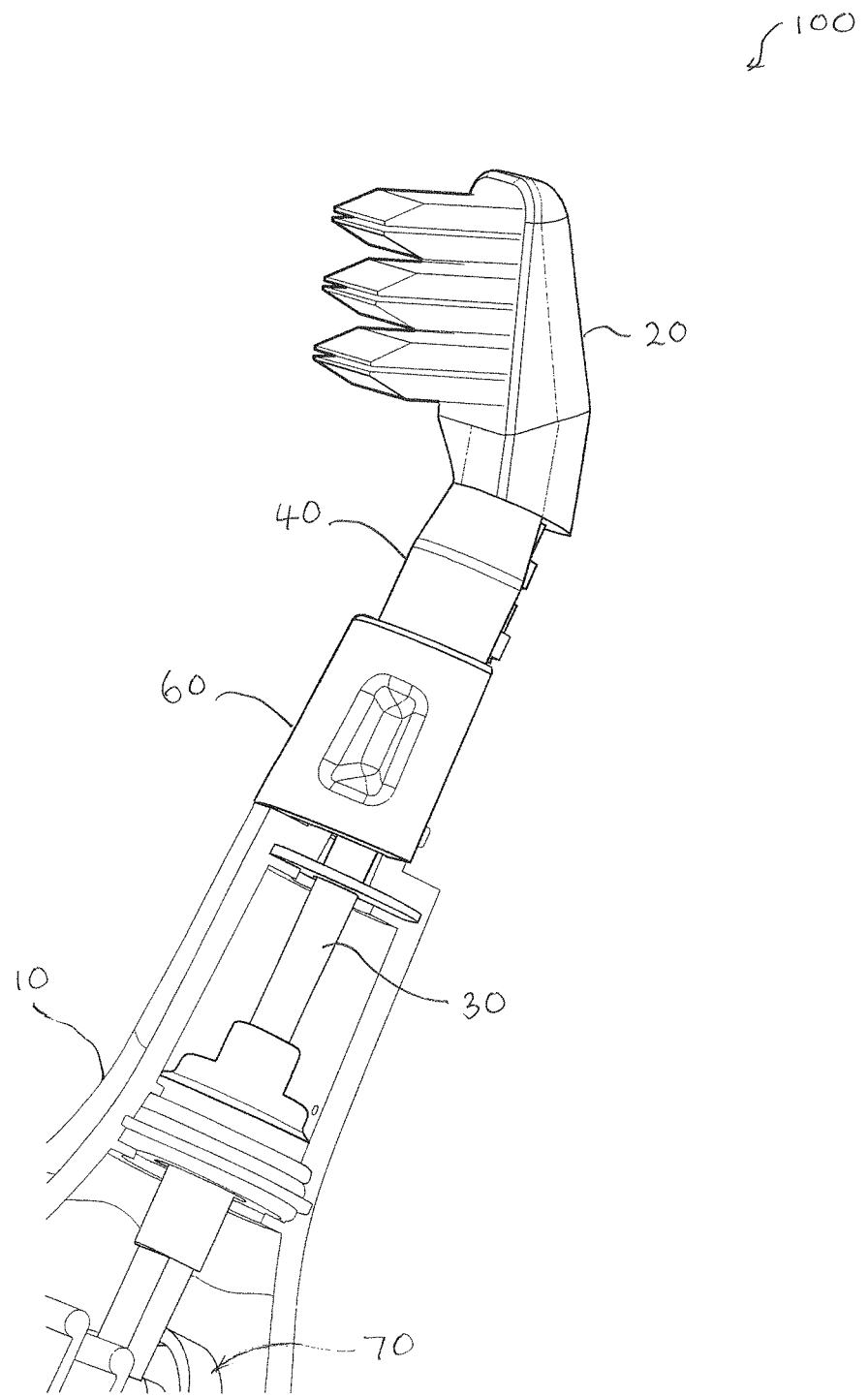
FIG. 2 is a perspective and partially cross-sectional view showing a part of the penetrating electric toothbrush of FIG. 1.

The disclosures of the U.S. patent application Ser. No. 11/379,862 for "Reciprocal Toothbrush" filed on Apr. 24, 2006, and the U.S. patent application Ser. No. 11/671,427 for "Electric Toothbrush" filed on Feb. 5, 2007, all by the inventor, are incorporated by reference as if fully set forth herein.

FIGS. 1-8 show an penetrating electric toothbrush 100 according to an embodiment of the invention.

The penetrating electric toothbrush 100 includes a handle 10, a replaceable brush head 20, a reciprocating bar 30, a head unit base 40, an engaging device 50, a selection device 60, and an actuator 70.

The handle 10 has an upper portion and a lower portion.

Figures 7, 8:
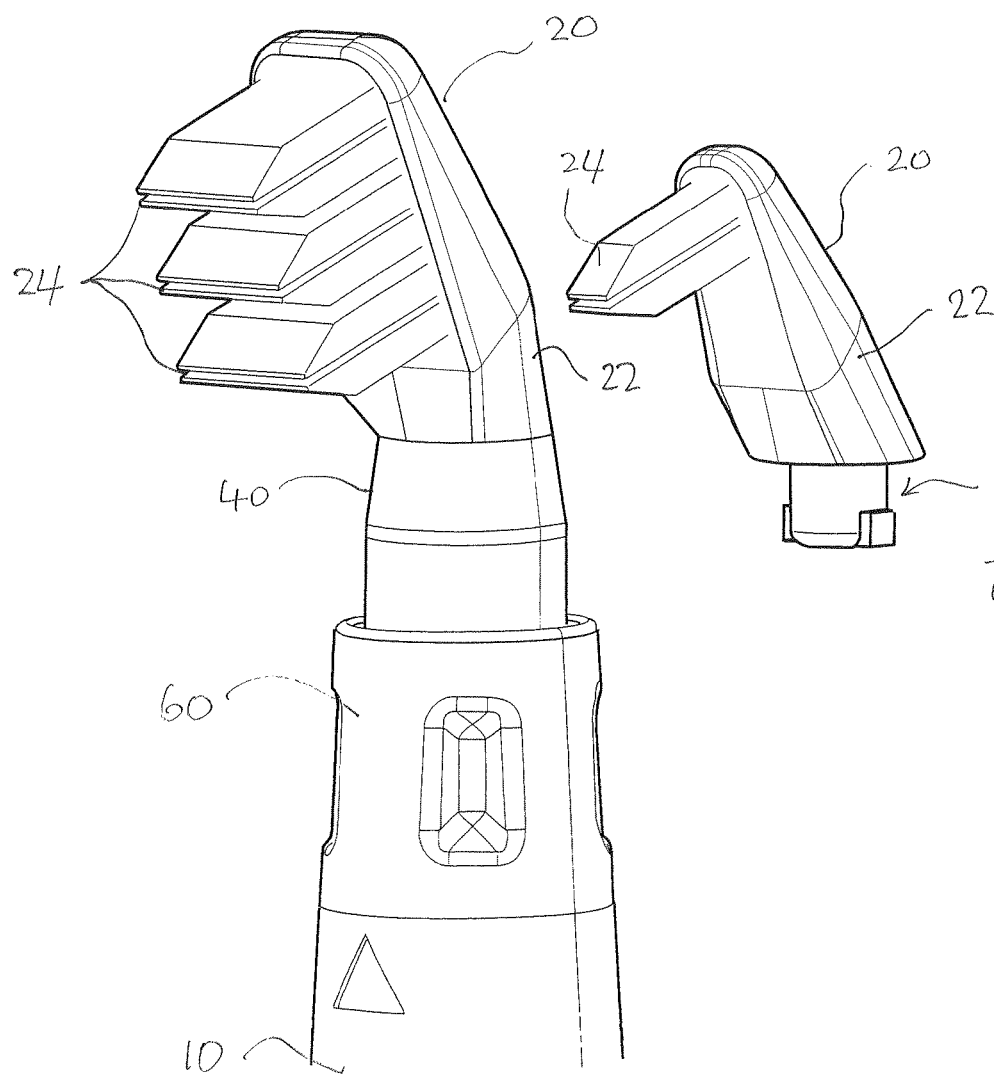
FIG. 7 is a perspective view showing an upper portion of the penetrating electric toothbrush of FIG. 1.
FIG. 8 is a perspective view showing a head unit base of the penetrating electric toothbrush of FIG. 1.

The replaceable brush head 20 comprises a head body 22, a plurality of bristles 24 fixed to the head body 22, and a detachable fastener 26 as shown in FIGS. 7 and 8.

The reciprocating bar 30 is provided inside the handle 20.

The head unit base 40 has a head receptacle portion 42, a actuator receiving recess 44, and a bar guiding portion 46. The reciprocating bar 30 is protruded from the handle 10 and received in the actuator receiving recess 44, and the actuator receiving recess 44 is configured to engage the reciprocating bar 30 in either penetration mode or polishing mode.

The engaging device 50 is disposed at an end of the reciprocating bar 30 and engaging the head unit base 40 with the reciprocating bar 30 so that the brush head 20 and the head unit base 40 move relative to the reciprocating bar 30 in either penetration mode or polishing mode.

The selection device 60 places the engaging device 50 either in the penetration mode or the polishing mode.

The actuator 70 is disposed inside the handle 10 and moves the reciprocating bar 30 back and forth.

The brush head 20 moves together with the reciprocating bar 30 in the polishing mode. The brush head 20 is free to move relative to the reciprocating bar 30 within a predetermined distance in the penetration mode, and the longitudinal axis of the brush head 20 is inclined from the longitudinal axis of the handle 10 with a predetermined angle.

The head receptacle portion 42 of the head unit base 40 may be configured to receive, lock, unlock, and release the replaceable brush head 20.

The handle 10 may comprise a connecting sleeve 11 that is provided on the end of the handle 10 that is adjacent to the selection device 60, and the selection device 60 comprises: a selection sleeve 62 provided between the handle 10 and the head unit base 40 and surrounding the connecting sleeve 11 of the handle 10; a selection groove 64 provided inside the selection sleeve 62; and a selection protrusion 12 that is provided on the connecting sleeve 11 and receives the selection groove 64.

The selection protrusion 12 may comprise an angularly spaced mode recess that keeps to move the mode change lever into the polishing mode or the penetration mode.

The bar guiding portion 46 may be provided at a lower portion of the head unit base 40.

The bar guiding portion 46 may provide a cylindrical hole 46A for allowing a portion of the reciprocating bar 30 to move there through.

The bar guiding portion 46 of the head unit base 40 may comprise a plurality of engaging protrusions 46B on outside, and the plurality of engaging protrusions 46B may be enclosed by the selection sleeve 62 and engage therewith.

The engaging device 50 may comprise an arrow-shaped protrusion 52, and the actuator receiving recess 44 may comprise an arrow-shaped groove 45 for receiving and locking the arrow-shaped protrusion 52. The arrow-shaped protrusion includes a first two surfaces meeting each other with an angle smaller than 90 degrees and a second two surfaces meeting each other with an angle larger than 90 degrees so as to form a wedge-shaped point.

Figure 6:
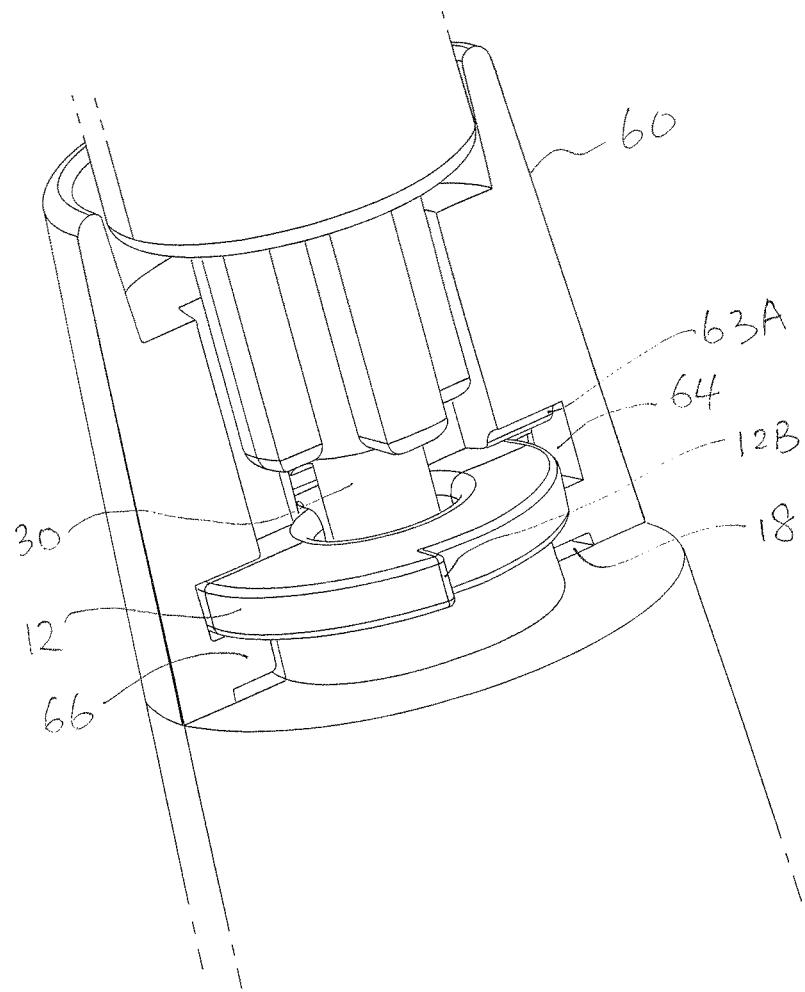
FIG. 6 is another perspective and partially cut-out view showing selection device of the penetrating electric toothbrush of FIG. 1.

The selection sleeve 62 of the selection device 60 may further comprise an engaging protrusion 66, and the handle 10 may further comprise an engaging groove 18 provided around the upper portion of the handle 10. The engaging protrusion 66 and the engaging groove 18 may connect the selection sleeve 62 and the handle 10 movably as shown in FIGS. 6 and 7.

Figure 9:
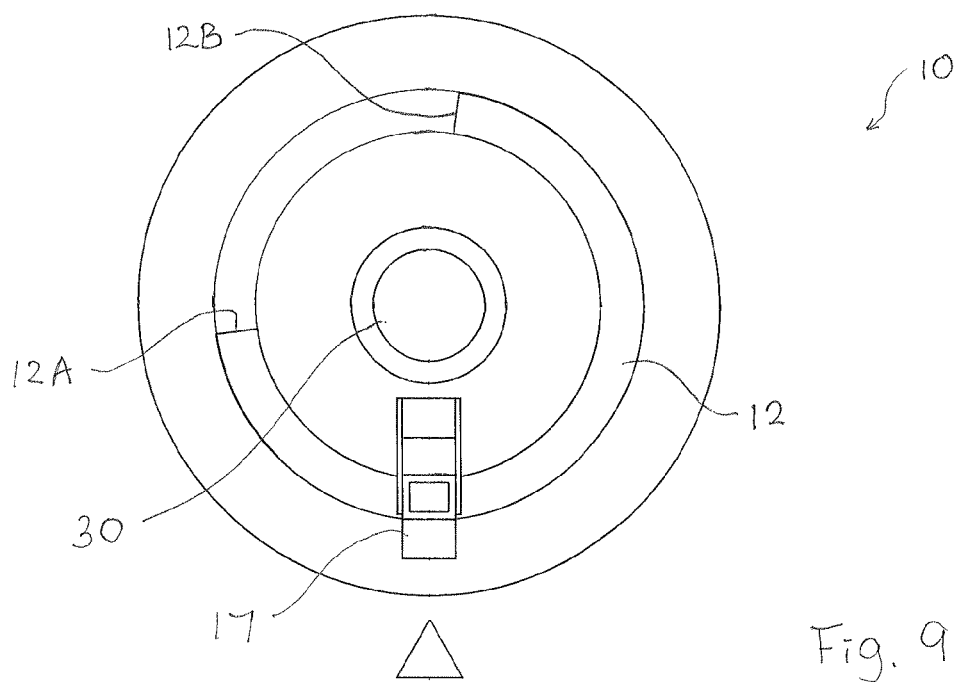
FIG. 9 is a top plan view showing an upper portion of a handle according to an embodiment of the invention.

The selection sleeve 62 of the selection device 60 may further comprise locking recesses 63A, 63B in an upper portion of the selection groove 64. The selection device 60 may further comprise a locking protrusion 17 that is received by the locking recesses 63A or 63B in each mode, by which the locking is achieved. The locking recesses 63A, 63B are apart from each other by about 90 degrees as shown in FIG. 9. The locking protrusion 17 is actually provided integrally with the selection protrusion 12, and may have a shape of a toppled U, which has an elasticity such that the top end is clicked into the locking recesses 63A, 63B for each mode. Of course, the locking protrusion 17 may have other shapes having an elasticity vertically, which can be clicked into the locking recess 63A, 63B.

Figure 3:
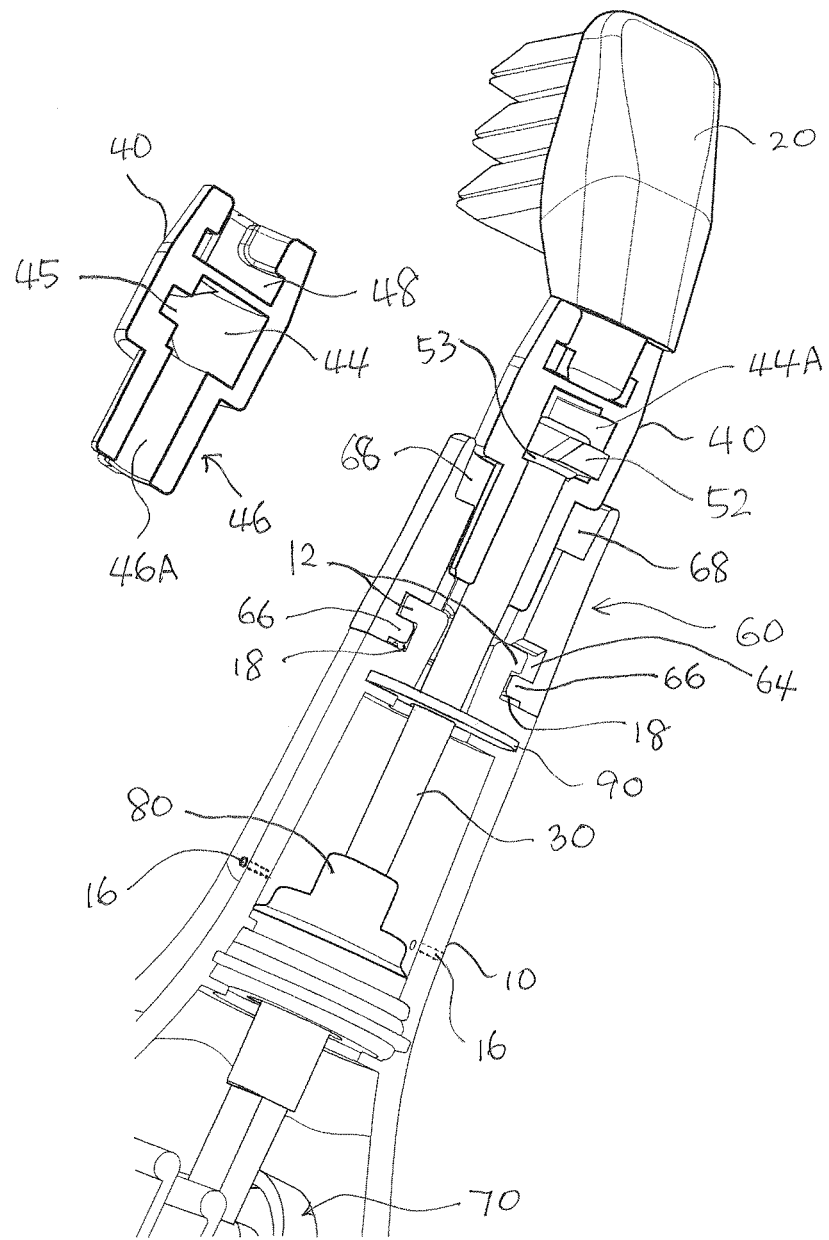
FIG. 3 is another perspective and partially cross-sectional view of a part of the penetrating electric toothbrush of FIG. 1.
Figure 4:
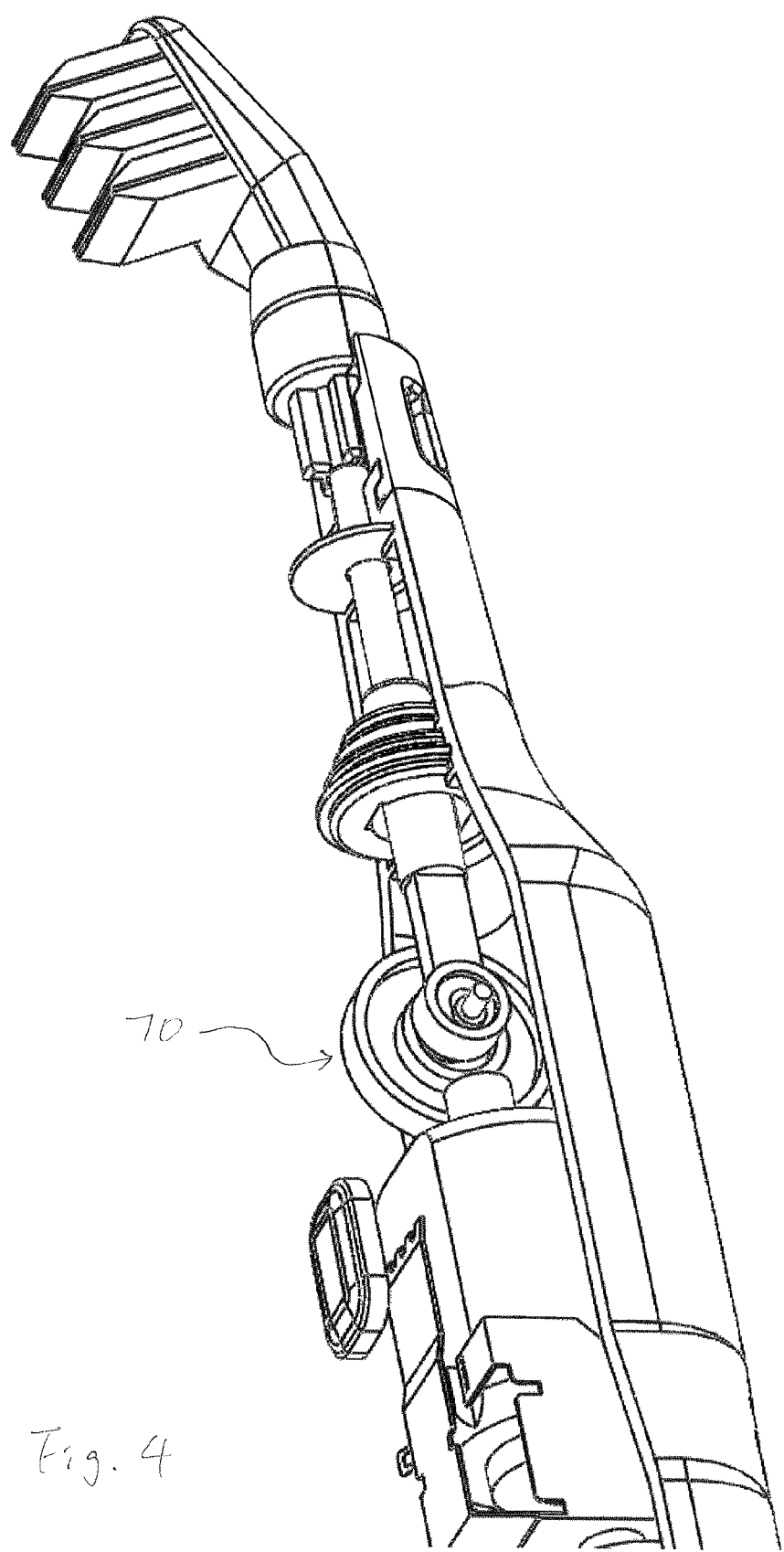
FIG. 4 is an elevation and partially cut-out view of a part of the penetrating electric toothbrush of FIG. 1.

The electric toothbrush 100 may further comprise a water proofing rubber sleeve 80 provided around the reciprocating bar 30 in the upper portion of the handle 10 for preventing water from the lower portion of the handle 10 as shown in FIG. 3.

The electric toothbrush 100 may further comprise an axis slider ring 90 provided around the reciprocating bar 30 in the upper portion of the handle 10 above the water proofing rubber sleeve 80 for limiting and guiding the movement of the reciprocating bar 30 and a perimeter of the axis slider ring 90 may be fixed inside the handle 10 as shown in FIG. 3.

The upper portion of the handle 10 may comprise two or more holes 16 for removing water from inside of the handle 10, and the holes 16 may be provided right above the water proofing rubber sleeve 80. The position, shape, and size of the holes 16 may be adjusted accordingly.

The axis slider ring 90 may be made of metal.

The selection sleeve 62 may further comprise an annular gap 68 for allowing an outer portion of the head unit base 40 to move freely and without a pinching gap between the head unit base 40 and the selection sleeve 62 as shown in FIG. 3.

The head unit base 40 may further comprise an L-shape fastening groove 48 adapted to fix the replaceable brush head 20 as shown in FIG. 3. The detachable fastener 26 is pushed in from the above of, twisted by a predetermined angle (preferably 90 degrees), fit into, and locked with the L-shape fastening groove 48.

The engaging device 50 comprises a step portion 53 under the engaging device 50, which prevents it out of the actuator receiving recess 44.

In FIG. 3, the gap 44A is a remaining space of the receiving recess 44 when the arrow-shaped protrusion 52 is locked in the an arrow-shaped groove 45. The gap 44A works a gap through which the reciprocating bar 30 can move when the arrow-shaped protrusion 52 is not locked in the an arrow-shaped groove 45.

Figure 10:
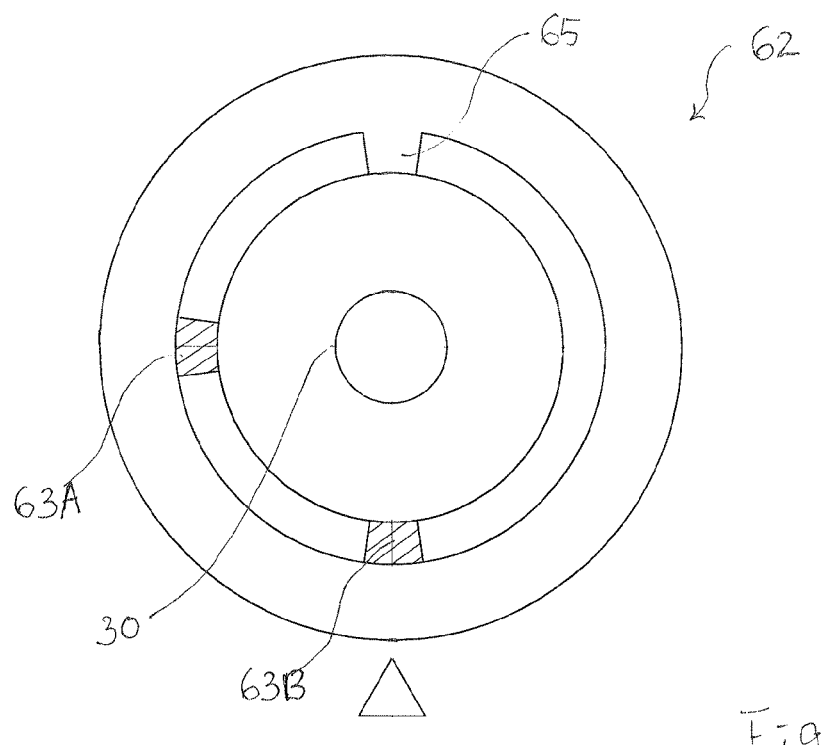
FIG. 10 is a cross-sectional view showing a lower portion of a selection sleeve at about a level of selection protrusion according to an embodiment of the invention.

FIGS. 9 and 10 show how the handle 10 and the selection sleeve 62 engage each other around the selection device 60.

In certain embodiment of the invention, the selection sleeve 62 may further comprise a mode change lever 65 provided toward inside of the selection sleeve 62, so as to limit the relative rotation of the selection sleeve 62 and the handle 10. The mode change lever 65 is stopped by a stopping edge 12A or 12B provided in the selection protrusion 12.

When the locking protrusion 17 is clicked into the locking recess 63B, then the mode change lever 65 contacts the stopping edge 12B, to be stopped, as can be seen in FIGS. 9 and 10. Similarly, when the locking protrusion 17 is clicked into the locking recess 63A, then the mode change lever 65 contacts the stopping edge 12A, to be stopped.

The selection sleeve 62 in FIG. 10 is assembled on the top of the handle 10 in FIG. 9. Then the locking protrusion 17 is clicked into and locked to the locking recess 63B. If rotating the selection sleeve 62 by about 90 degrees counterclockwise while holding the handle 10, the locking protrusion 17 is disengaged out of the locking recess 63B, and engaged with the locking recess 63A.

Figure 5:
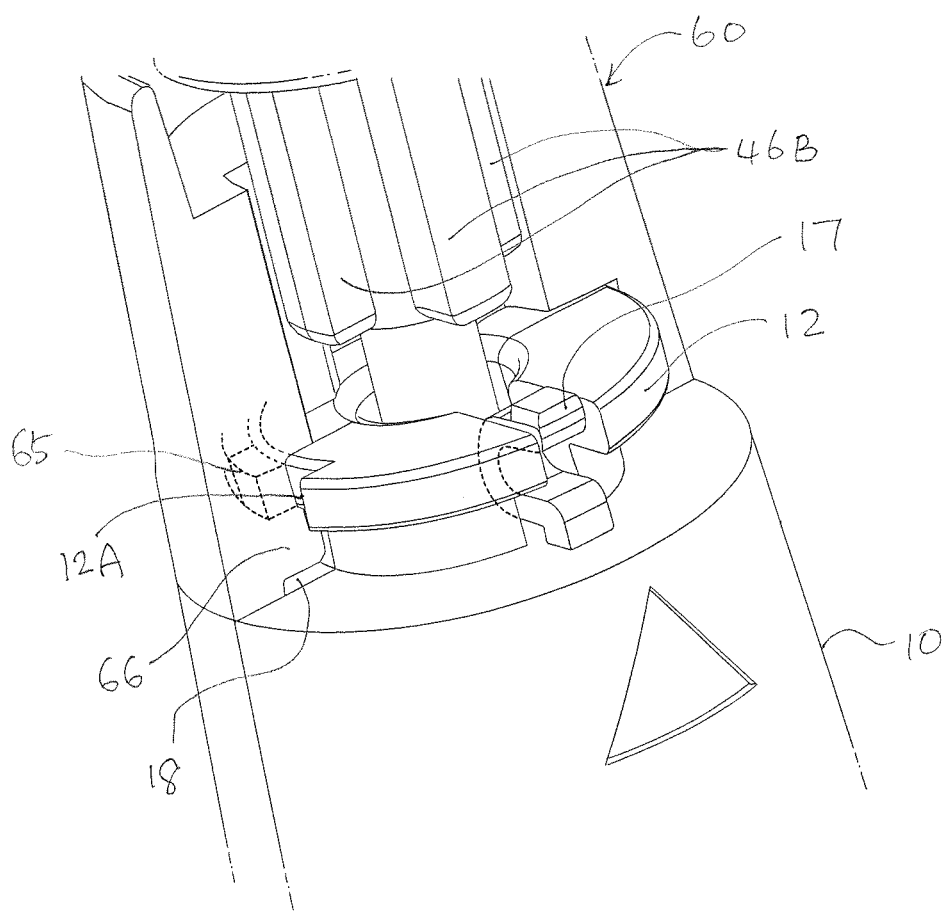
FIG. 5 is a perspective and partially cut-out view showing selection device of the penetrating electric toothbrush of FIG. 1.

In FIG. 5, the selection sleeve 62 is rotated counterclockwise by about 20 degrees from the state of FIG. 10.

In FIG. 6, only the rear half of the locking recesses 63A is shown. The front half of the selection sleeve 62 is going to have the other half the locking recesses 63A.

The operation of the electric toothbrush is further explained referring chapters 5 and 6 of "Introduction to Mechanisms", Rapid Design through Visual and Physical Prototyping, Carnegie Mellon University (http://www.cs.cmu.edu/~rapidproto/mechanisms/).

Action of plate cam with a follower rod fixed to an offset point on disk, creates output motion of both translational and oscillatory motion at the opposite end of the follower that is aligned along a longitudinal axis (6.1.1 Last sentence in paragraph.) The follower, at its midpoint, slides through a guide at the nose of the body, or handle, which encases the motorized cam mechanism. The output motion can be described in the following two ways: The relative midpoint of the follower moves through a rubber ring guide, which lines the nose of the body, in translational (up and down) motion, which directly follows the rotational motion of the cam. The follower, at its vertical tip, also sees oscillatory (back and forth, or chopping) motion that is reciprocal to the rotational motion of the cam; the follower behaves as a planar rocker through guide (5.1.2 Functions of Linkages.)

A section near the vertical tip of the follower rod is cut with two distinct grooves on two adjacent quarter sides of the rod. First quarter of the rod is cut with a female groove that mates with a fixed male screw that protrudes into the cylindrical hollow within the body of the brush-head. In this position (A), the brush-head locks into the mated groove of the follower rod. The adjacent quarter of the rod is cut with a longitudinally elongated female groove in where the male screw is free to move or slide longitudinally along the length of this elongated groove. In this position (B), the follower rod is free to slide within (the cylindrical hollow inside) the body of the brush-head, only limited by the predetermined length of the female groove, which allows the male screw movement. The latter position (B) creates independent, however limited, movement, or play, in the longitudinal or translational motion between the follower rod and the brush-head.

In the locked position (A), the orientation of the bristles on the brush-head stands perpendicular to the oscillatory output motion thereby utilizing primarily the translational output motion of the follower and creating a sweeping, or polishing effect in one plane in respect to the contact point, or face, of the bristles. In position B, the orientation of the bristles is, or stands, in-line with the oscillatory output motion thereby following this to-and-fro motion that creates a chopping or digging movement that is multi-planar in respect to the contact point of the bristles.

In this position (B), the oscillatory motion of the bristles is coupled with the freely sliding effect between the body of the brush-head and the follower, allowing for variable translational position of the brush-head that creates a virtual suspended state, or floating of the brush-head in midair as the cam rotates at high frequency. With this slight, but variable instantaneous positioning of the brush-head from the high velocity in oscillatory and translational motion (with play), the bristles achieve a digging effect that can instantaneously conform to minute changes in contact surface; thus ultimately producing thorough penetrating effect deep within the gum-line.

Unlike all other mechanical devices that have fixed linkages that rigidly follow the rotation of a driving mechanism, this invention harnesses a free, variable movement within its mechanics to achieve an organic element to its output motion. This element of the invention is critical to effective bristle placement for complete hygiene by adapting to the organic form and minute spaces that constitutes most critical and important areas of the tooth and gum.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. An electric toothbrush comprising:
    a handle having an upper portion and a lower portion;
    a replaceable brush head comprising a head body, a plurality of bristles fixed to the head body, and a detachable fastener;
    a reciprocating bar provided inside the handle;
    a head unit base having a head receptacle portion, an actuator receiving recess, and a bar guiding portion, wherein the reciprocating bar is protruded from the handle and received in the actuator receiving recess, wherein the actuator receiving recess is configured to engage the reciprocating bar in either penetration mode or polishing mode;
    an engaging device disposed at an end of the reciprocating bar and engaging the head unit base with the reciprocating bar so that the brush head and the head unit base move relative to the reciprocating bar in either penetration mode or polishing mode;
    a selection device that places the engaging device either in the penetration mode or the polishing mode; and
    an actuator that disposed inside the handle and moves the reciprocating bar back and forth,
    wherein the brush head moves together with the reciprocating bar in the polishing mode, wherein the brush head is free to move relative to the reciprocating bar within a predetermined distance in the penetration mode, wherein the longitudinal axis of the brush head is inclined from the longitudinal axis of the handle with a predetermined angle,
    wherein the handle comprises a connecting sleeve that is provided on the end of the handle that is adjacent to the selection device,
    wherein the selection device comprises:
    a selection sleeve provided between the handle and the head unit base and surrounding the connecting sleeve of the handle;
    a selection groove provided inside the selection sleeve; and
    a selection protrusion that is provided on the connecting sleeve and receives the selection groove,
    wherein the selection protrusion comprises four angularly spaced mode recesses that keep the selection groove either in the polishing mode or the penetration mode,
    wherein the bar guiding portion is provided at a lower portion of the head unit base,
    wherein the bar guiding portion of the head unit base comprises a plurality of engaging protrusions on outside, wherein the plurality of engaging protrusions are enclosed by the selection sleeve and engage therewith, and
    wherein the engaging device comprises an arrow-shaped protrusion and the actuator receiving recess comprises an arrow-shaped groove for receiving and locking the arrow-shaped protrusion, wherein the arrow-shaped protrusion includes a first two surfaces meeting each other with an angle smaller than 90 degrees and a second two surfaces meeting each other with an angle larger than 90 degrees so as to form a wedge-shaped point, wherein a gap is formed in a remaining space of the receiving recess when the arrow-shaped protrusion is unlocked in the arrow-shaped groove, such that the gap works as a gap through which the reciprocating bar can move when the arrow-shaped protrusion is not locked in the arrow-shaped groove,
    wherein the selection sleeve of the selection device further comprises locking recesses in an upper portion of the selection groove, wherein the selection device further comprise a locking protrusion that is received by one of the locking recesses in each mode, by which the locking is achieved, wherein the locking recesses are apart from each other by about 90 degrees,
    wherein the engaging device comprises a step portion under the engaging device for preventing the engaging device and the end of the reciprocating bar out of the actuator receiving recess.

2. The electric toothbrush of claim 1, wherein the head receptacle portion of the head unit base is configured to receive, lock, unlock, and release the replaceable brush head.

3. The electric toothbrush of claim 1, wherein the bar guiding portion provides a cylindrical hole for allowing a portion of the reciprocating bar to move.

4. The electric toothbrush of claim 1, wherein the selection sleeve of the engaging device further comprises a locking protrusion, wherein the handle further comprises a locking groove provided around the upper portion of the handle, and wherein the locking protrusion and the locking groove connect the selection sleeve and the handle movably.

5. The electric toothbrush of claim 1, further comprising a water proofing rubber sleeve provided around the reciprocating bar in the upper portion of the handle for preventing water from the lower portion of the handle.

6. The electric toothbrush of claim 5, further comprising an axis slider ring provided around the reciprocating bar in the upper portion of the handle above the water proofing rubber sleeve for limiting and guiding the movement of the reciprocating bar.

7. The electric toothbrush of claim 6, wherein the upper portion of the handle comprises two or more holes for removing water from inside, and wherein the holes are provided right above the water proofing rubber sleeve.

8. The electric toothbrush of claim 6, wherein the axis slider ring is made of metal.

9. The electric toothbrush of claim 1, wherein the selection sleeve further comprises an annular gap for allowing an outer portion of the head unit base to move freely and without a pinching gap between the head unit base and the selection sleeve.

10. The electric toothbrush of claim 1, wherein the head unit base further comprises an L-shape fastening groove adapted to fix the replaceable brush head.

* * * * *